United States Patent [19]
Van Der Puy

[11] Patent Number: 6,111,130
[45] Date of Patent: Aug. 29, 2000

[54] PROCESS FOR THE PREPARATION OF TRIFLUOROMETHYL CONTAINING DERIVATIVES

[75] Inventor: Michael Van Der Puy, Erie County, N.Y.

[73] Assignee: AlliedSignal Inc., Morristown, N.J.

[21] Appl. No.: 09/307,819

[22] Filed: May 10, 1999

Related U.S. Application Data

[60] Provisional application No. 60/085,448, May 14, 1998.

[51] Int. Cl.$^7$ .................................................. C07C 69/76
[52] U.S. Cl. .................... 560/111; 560/122; 560/123; 560/124; 560/223; 560/261; 560/262; 560/102; 568/842; 568/843
[58] Field of Search ..................... 560/102, 111, 560/122, 123, 124, 223, 261, 262; 568/842, 843

[56] References Cited

U.S. PATENT DOCUMENTS

| | | | |
|---|---|---|---|
| 5,446,217 | 8/1995 | Van Der Puy et al. | 570/156 |
| 5,532,419 | 7/1996 | Van Der Puy et al. | 570/167 |
| 5,654,473 | 8/1997 | Van der Puy | 560/262 |

OTHER PUBLICATIONS

F. Jin et al., "Trifluoroacetyltriphenylsilane As A Potentially Useful Fluorine–Containing Building Block. Preparation And Its Transformation Into 2,2–Difluoro Enol Silyl Ethers", Tetrahedron Letters, vol. 33, No. 9, pp. 1221–1224, (1992).

B. Jiang et al., "Palladium–Catalyzed Cross–Coupling Of Trifluoroisopropenylzinc Reagent With Vinyl Halides. A Novel Stereospecific Snythesis If Trifluoromethylated 1,3–Dienes", Tetrahedron Letters, vol. 33, No. 4, pp. 511–514, (1992).

T. Hiyama et al., "A Facile and Practical Synthesis of 1–Aryl–3,3,3,–trifluoropropynes", The Chemical Society of Japan, Bull. Chem. Soc. Jpn, 60, 4385–4394 (1987).

M. Van Der Puy et al., "Preparation, fluorination and synthetic utility of a CFC–olefin adduct", Journal of Fluorine Chemistry, 76, 49–54 (1996).

Patent Abstract of Japan, JP 62228032 A, Oct. 6, 1987, (Sagami Chem Res Centre).

M. Van Der Puy et al., "Preparation, fluorination and synthetic utility of a CRC–olefin adduct", Journal of Fluorine Chemistry 76 (1976) 49–54.

P. Piccardi et al., "The Peroxide–Initiated Addition of 1,1–Dibromotertrafluoroethane to Ethylene Propene, and 2–Methylpropene", Journal of The Chemical Society JCPRB4(9/10) (1972) 1121–1290.

R. Davis et al., "Chemical Properties Of The Nobel Gases", Principles of Chemistry, 21–3, p. 700, (1938).

A. Laurent et al., "Synthesis of Trifluoromethylalkenes and Alkynes, Trifluoromethyl Captodative Olefins", Tetrahedron Letters, vol. 32, No. 26, pp. 3071–3074, (1991).

M. Fujita et al., "Practical, Stereocontrolled Synthesis of Polyfluorinated Artificial Pyrethroids", The Chemical Society of Japan, Bull. Chem. Soc. Jpn, 60, 4385–4394 (1987).

T. Umemoto et al., "New Method for Trifluoromethylation of Enolate Anions and Applications to Regio–, Diastereo– and Enantioselective Trifluoromethylation", Journal of Organic Chemistry, (1994),59,5692–5699.

C. Ates et al., "Trifluoroethylidenation of Compounds with Activated Methylene Groups", Tetrahedron Letters, vol. 34, No. 36, pp. 5711–5714, (1993).

*Primary Examiner*—Paul J. Killos
*Attorney, Agent, or Firm*—Colleen D Szuch; Marie Colluzo

[57] ABSTRACT

The present invention relates to a process for the preparation of trifluoromethylated derivatives of the formula $CF_3CCl=CHCH_2OC(=O)R$, wherein R is unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R', a phenyl group unsubstituted or substituted with R'; R' is an unsubstituted or substituted $C_1$ to $C_6$ straight chain or branched alkyl; and wherein where R and/or R' are substituted each is substituted with R', by reaction of HCFC-353 with carboxylic acid salts. The trifluoromethylated derivatives, particularly $CF_3CCl=CHCH_2OC(=O)CH_3$, are versatile intermediates for the synthesis of a wide variety of trifluoromethylated organic compounds, which find utility as pharmaceuticals, agricultural chemicals, and materials such as liquid crystals.

22 Claims, No Drawings

PROCESS FOR THE PREPARATION OF TRIFLUOROMETHYL CONTAINING DERIVATIVES

CROSS REFERENCE TO RELATED APPLICATION

Reference is made to and priority claimed from pending Provisional Patent Application Ser. No. 60/085,448 filed May 14, 1998.

FIELD OF THE INVENTION

The present invention relates to a process for the preparation of trifluoromethyl containing derivatives useful in the synthesis of trifluoromethylated organic compounds, particularly $CF_3CCl=CHCH_2OC(=O)CH_3$ and $CF_3CH_2CH_2CH_2OH$.

BACKGROUND OF THE INVENTION

Trifluoromethyl group containing derivatives such as $CF_3CCl=CHCH_2OAc$ and $CF_3CH_2CH_2CH_2OH$ are useful in the synthesis of fluorinated organic compounds having utility as pharmaceuticals, agricultural chemicals and materials such as liquid crystals. Traditionally, they have been prepared from 1,3-dichloro-4,4,4-trifluoro-2-butene ($CF_3CCl=CHCH_2Cl$) or HCFC-1343. U.S. Pat. No. 5,654,473, herein incorporated by reference in its entirety, discloses the preparation of a number of trifluoromethylated compounds from HCFC-1343. The synthesis of this starting material by the prior art methods is problematic in that high conversion is obtained at the sacrifice of selectivity. Thus, the drawbacks of the processes by which the intermediate is produced limit the useful yield of trifluoromethyl group containing derivatives.

The objective of the invention is to produce trifluoromethyl group containing derivatives by a process having higher yield and selectivity than the known processes.

DESCRIPTION OF THE INVENTION

The invention relates to a process comprising: reacting a compound of the formula $CF_3CCl_2CH_2CH_2Cl$ (HCFC-353) with a salt of a carboxylic acid in the presence of a polar aprotic solvent and under conditions sufficient to produce a compound of the formula $CF_3CCl=CHCH_2OC(=O)R$ wherein R is unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R', or a phenyl group unsubstituted or substituted with R'; wherein R' is an unsubstituted or substituted $C_1$ to $C_6$ straight chain or branched alkyl; and wherein when R and/or R' are substituted each is substituted with R'; and recovering a compound of the formula $CF_3CCl=CHCH_2OC(=O)R$.

When a carboxylic acid salt other than a lithium-based salt is used in the invention, $CF_3CCl_2CH=CH_2$ by-product is produced in a 1:2 ($CF_3CCl=CHCH_2OC(=O)R$) ratio. This by-product can be separated (by conventional means such as distillation) and isomerized with LiCl (See, VanDer-Puy et al., *Journal of Fluorine Chemistry*, 76 (1996) 49–54 which is incorporated herein by reference) to HCFC-1343 which readily reacts with the carboxylic acid salt in the presence of a polar aprotic solvent (See, U.S. Pat. No. 5,654,473) under conditions sufficient to produce a compound of the formula $CF_3CCl=CHCH_2OC(=O)R$. See Example 2.

When a lithium-based carboxylic acid salt is used, by-product formation is eliminated by in situ conversion to HCFC-1343 which readily reacts with the carboxylic acid salt in the presence of a polar aprotic solvent under conditions sufficient to produce a compound of the formula $CF_3CCl=CHCH_2OC(=O)R$.

The ability to convert the by-product ultimately to a compound of the formula $CF_3CCl=CHCH_2OC(=O)R$ after separation or via in situ conversion defines a great advantage over the prior art processes. With the process of the invention, a product mixture comprising >96% useful materials is obtained.

The HCFC-353 starting material may be produced as described in U.S. Pat. No. 5,532,419, herein incorporated by reference in its entirety by the addition reaction of ethylene and 1,1,1-trichloro-2,2,2-trifluoroethane in the presence of a catalyst and an inert solvent.

The lithium chloride used in the invention should be substantially anhydrous (i.e., it should contain less than about 5 weight percent water). This material is commercially available from most chemical suppliers (e.g., Aldrich). A catalytic amount of LiCl is used in the process. Typically, the LiCl is present in an amount of from about 2 to about 25 mole percent based on HCFC-1343.

Any carboxylic acid salt of the formula $R-COO^{31}M^+$ can be used in the invention wherein R is unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R', or a phenyl group unsubstituted or substituted with R'; wherein R' is an unsubstituted or substituted $C_1$ to $C_6$ straight chain or branched alkyl; and wherein when R and/or R' are substituted each is substituted with R'; and M is a Group IA metal. Preferably R is unsubstituted or substituted $C_1$ to $C_6$ straight chain or branched alkyl and most preferably R is $CH_3$. M is preferably lithium, sodium or potassium.

Any polar, aprotic solvent may be used in the invention provided it is capable of dissolving at least about 10 mole % of the carboxylic acid salt relative to HCFC-353. Suitable solvents include dimethylsulfoxide (DMSO), sulfolane, N-methylpyrrolidinone (NMP) and dimethylformamide (DMF). DMF and DMSO are preferred because the carboxylic acid salts are very soluble in these solvents. When solvents with lower solubility for the acid salts are used, phase transfer catalysis may be employed. This helps the reaction rate by bringing into the solvent phase the inorganic part of the salt which is otherwise too insoluble for a reasonable reaction rate. This might be useful for sulfolane or NMP where the solubility of the salt is generally less than in DMF or DMSO. Typically, the solvents are used in an amount sufficient to form about a 0.5 to about 3.0 M solution of HCFC-353, HCFC-1343 or $CF_3CCl_2CH=CH_2$.

The pressure at which the process is conducted is not critical. For convenience, the process is preferably conducted at atmospheric pressure in any convenient, suitable reaction vessel.

Generally, the reaction temperature will range from about 50° C. to about the boiling point of the polar aprotic solvent used in the process. With the preferred solvents, reaction temperatures range from about 50° C. to about 150° C. and preferably from about 85° C. to about 150° C. Under these conditions, reaction times vary from about 2 hours to about 48 hours, preferably from about 10 hours to about 24 hours.

The preferred $CF_3CCl=CHCH_2OC(=O)R$ compounds are generally liquids that can be purified by distillation. The ratio of the geometrical isomers produced is about 93 to about 97% of the major isomer to about 3 to about 7% of the minor isomer. After the reaction is complete, volatile products may be recovered from the reaction medium either by direct distillation, provided the boiling points of the products and solvent are well separated (e.g. with solvents such as sulfolane or N-methylpyrrolidinone), or the entire mixture may be diluted with water, the organic products extracted, and subsequently purified by distillation (e.g. with solvents such as DMF and dimethylsulfoxide).

The stoichiometry of the reaction requires that about 2 moles of carboxylic acid salt be reacted for every about 1 mole of HCFC-353 or HCFC-1343. Typically from about 2 to about 4 moles of the carboxylic acid salt are used per about 1 mole of HCFC-353 or HCFC-1343.

In another embodiment, the invention relates to a process for the production of a compound of the formula ($CF_3CCl=CHCH_2OC(=O)CH_3$) comprising reacting either sodium acetate or potassium acetate with HCFC-353 in DMF at a temperature of from about 50° C. to about 150° C., optimally between about 65° C. to about 85° C. for a time sufficient to produce $CF_3CCl=CHCH_2OC(=O)CH_3$ Several other useful compounds can be prepared from $CF_3CCl=CHCH_2OC(=O)R$. Consequently, this invention provides, by extension, an improved process for their manufacture too. For example, $CF_3CH_2CH_2CH_2OH$ can be prepared from $CF_3CCl=CHCH_2OC(=O)R$ via hydrolysis, followed by reduction. See, U.S. Pat. No. 5,654,473. Thus, in yet another embodiment, the invention relates to a process comprising (1) hydrolyzing $CF_3CCl=CHCH_2OC(=O)R$ with a base in the presence of a solvent to produce $CF_3CCl=CHCH_2OH$; (2) reducing $CF_3CCl=CHCH_2OH$ with hydrogen in the presence of a hydrogenation catalyst and a base to produce $CF_3CH_2CH_2CH_2OH$; and recovering $CF_3CH_2CH_2CH_2OH$.

The first process step is exothermic and proceeds quickly, thus, cooling may be necessary to control the reaction. Reaction times for the first step are typically less than or equal to about one hour at a temperature of about 35° C. Any solvent in which the base is soluble may be used in the first process step. Suitable solvents include lower molecular weight alcohols such as methanol, tetrahydrofuran, water, and mixtures thereof Any base known to be useful in the hydrolysis of halogenated acetates may be used in the first step of the process. Suitable bases include, but are not limited to, potassium or sodium hydroxide.

The second process step proceeds smoothly under mild conditions (i.e., hydrogen pressures of from about 1 to about 10 atmospheres and temperatures in the range of from about 30° C. to about 100° C.). Suitable hydrogenation catalyst include, but are not limited to, Pd, Pt, and Rh supported on carbon or alumina. These catalysts are commercially available, alternately they may be made by methods known in the art. The catalyst is used in an amount of from about 1 to about 10 mg per gram of solvent. The catalyst loadings range from about 1 to about 20%, preferably from about 5 to about 10%.

A base is used (e.g. sodium acetate) in the second process step to prevent the reaction medium from becoming too acidic (i.e., pH<2), since under highly acidic conditions, the hydroxyl group can undergo hydrogenolysis, forming $CF_3CCl=CHCH_3$. The base is generally present in an amount of from about 1 to about 2 equivalents relative to the starting material.

One of ordinary skill in the art will recognize the versatility of the process of the invention to prepare other trifluoromethylated intermediates useful in synthesizing trifluoromethylated organic compounds.

EXAMPLES

Example 1

This example demonstrates the preparation of $CF_3CCl_2CH=CH_2$ and $CF_3CCl=CHCH_2OAc$ from HCFC-353. A mixture of sodium acetate (300 g), dimethylformamnide (750 mL), and HCFC-353 (323 g, 1.5 mol) were heated to 70–75° C. with mechanical stirring for 40 hours. The conversion was >99%. The cooled mixture was poured into 2 liters of ice and water. The lower layer was separated, and the aqueous layer extracted with 2×200 mL portions of ether. The combined organic layers were washed with water, brine, dried, and distilled to give 76.6 g (0.43 mol) $CF_3CCl_2CH=CH_2$ and 173.0 g (0.85 mol) of 96% pure $CF_3CCl=CHCH_2OAc$. Prior to distillation, a typical crude product mixture has the following composition: 32.93% $CF_3CCl_2CH=CH_2$, 1.24% $CF_3CHClCH=CHCl$, 0.33% $CF_3CCl=CHCH_2Cl$, 1.62% HCFC-353, and 63.47% $CF_3CCl=CHCH_2OAc$.

Comparative Example 1

Comparative Examples 1–3 demonstrate the importance of using the preferred solvents (i.e., solvents in which the carboxylic acid salt is at least 10% soluble relative to HCFC-353). Sodium acetate (100 g), $CF_3CCl_2CH_2CH_2Cl$ (100 g), and methanol (600 mL) were mixed and refluxed for 3 hours. Negligible reaction had occurred by GC analysis.

Comparative Example 2

The reaction was conducted and the reaction product was analyzed in the same manner as in Comparative Example 1 except that water was used instead of methanol. The reaction similarly failed to convert any of the starting material.

Comparative Example 3

Sodium acetate (25 g), 75 mL triglyme, and 20 g $CF_3CCl_2CH_2CH_2Cl$ were heated to 106° C. for 17 hours. The conversion of starting material was only about 3% by GC analysis.

Comparative Example 4

Comparative Example 4 is illustrative of the prior art in which HCFC-353 is converted to HCFC-1343 and by-product, $CF_3CHClCH=CHCl$. This by-product which is produced in significant quantity, does not produce $CF_3CCl=CHCH_2OAc$ on reaction with sodium acetate, and consequently represents a yield loss. Sodium methoxide (135.0 g, 2495 mol) in 550 ml methanol was added over 100 minutes with mechanical stirring to 411.0 g (1.907 mol) HCFC-353 in 200 ml MeOH at 0–10° C. Stirring was continued for 20 hours and the reaction mixture poured into 3 L water. The lower product layer was washed twice with 100 ml water and dried ($Na_2SO_4$), providing 308.1 g of crude product. Distillation gave 6.0 g forerun, 133.2 g of $CF_3CCl_2CH=CH_2$, 94.7 g of a mixture of $CF_3CHClCH=CHCl$ and $CF_3CCl=CHCH_2Cl$, 20.7 g starting material $CF_3CCl_2CH_2CH_2Cl$, 33 g. intermediate cuts and 16.1 g pot residue. Thus, the combined yield of dehydrochlorination products, $CF_3CCl_2CH=CH_2$, $CF_3CHClCH=CHCl$ and $CF_3CCl=CHCH_2Cl$, based on unrecovered starting material was 70%. The ratio of $CF_3CCl_2CH=CH_2$ : $CF_3CHClCH=CHCl$ : $CF_3CCl=CHCH_2Cl$ was 59:35:7 as determined by GC and $^{19}F$ NMR data.

Example 2—Recycle of $CF_3CCl_2CR=CH_2$ to improve the yield of $CF_3CCl=CHCH_2OAc$.

90.4 g (0.505 mol) of $CF_3CCl_2CH=CH_2$ produced by the reaction reported in Example 1 and 3.0 g LiCl were dissolved in 150 mL DMF and heated to 95–105° C. for 3 hours. The mixture was allowed to cool to 80° C. before adding 45 g sodium acetate, followed by stirring 1 hour at 80° C. The cooled mixture was poured into 400 mL water, and worked up as described in Example 1 (2×150 mL extractions with ether). Distillation gave 86.1 g (0.43 mol) of 97% pure $CF_3CCl=CHCH_2OAc$. Thus with recycle, the overall distilled yield of $CF_3CCl=CHCH_2OAc$ from HCFC-353 is 81%.

Example 3—Preparation of $CF_3CH_2CH_2CH_2OH$.

A solution of 8.0 grams NaOH in 30 nL water was added, over 1 hour, to 40.6 g of $CF_3CCl=CHCH_2OC(O)CH_3$ in 40 mL methanol, keeping the temperature less than 35° C. with the use of a water bath. After 1 hour, the mixture was diluted with 100 mL water. The lower layer was separated and the aqueous layer extracted with 2×50 mnL ether. The combined organic layers were washed with 25 mnL brine, dried ($Na_2SO_4$), and distilled to give 26.9 g (84% yield) of 99.7% pure $CF_3CCl=CHCH_2OH$.

A 375 mL glass pressure vessel was charged with 16.1 g (0.10 mole) of 3-chloro-4,4,4-trifluorobut-2-en-1-ol (obtained above), 9.8 g (0.1 mole) potassium acetate, 30 mnL methanol, and 55 mg 5% Pd/C catalyst. Hydrogenation was carried out at 45–50° C. and at an operating hydrogen pressure of 40–60 psi, adding hydrogen as needed until the theoretical quantity had been taken up (about 14 hours). The mixture was cooled and filtered. The filtrate was poured into 150 mL water and extracted 4×50 mL ether. The combined ether layers were washed with 50 mnL bicarbonate solution and dried (MgSO4). Distillation gave 9.4 g (73% yield) of 97% pure 4,4,4-trifluorobutan-1-ol.

What is claimed is:

1. A process to produce a compound of the formula $CF_3CCl=CHCH_2OC(=O)R$ wherein R is unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R', or a phenyl group unsubstituted or substituted with R'; wherein R' is an unsubstituted or substituted $C_1$ to $C_6$ straight chain or branched alkyl; and wherein when R and/or R' are substituted each is substituted with R' comprising reacting $CF_3CCl_2CH_2CH_2Cl$ with a compound of the formula $R-COO^{31}M^+$ wherein R is as defined above and M+ is a Group IA metal in the presence of a polar aprotic solvent.

2. The process of claim 1 wherein the $CF_3CCl=CHCH_2OC(=O)R$ is recovered.

3. The process of claim 1 wherein M+ is selected from the group consisting of lithium, sodium and potassium.

4. The process of claim 1 wherein M+ is lithium.

5. The process of claim 1 wherein M+ is not lithium and $CF_3CCl_2CH=CH_2$ is produced as a by-product.

6. The process of claim 5 further comprising separating $CF_3CCl_2CH=CH_2$; reacting $CF_3CCl_2CH=CH_2$ with LiCl to produce $CF_3CCl=CHCH_2Cl$; reacting $CF_3CCl=CHCH_2Cl$ with a compound of the formula $R-COO^-M^+$ wherein R is unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R', or a phenyl group unsubstituted or substituted with R'; wherein R' is an unsubstituted or substituted $C_1$ to $C_6$ straight chain or branched alkyl; and wherein when R and/or R' are substituted each is substituted with R' and M+ is a Group IA metal in the presence of a polar aprotic solvent.

7. The process of claim 5 wherein the $CF_3CCl=CHCH_2OC(=O)R$ is recovered.

8. The process of claims 1, 3, 5 or 6 wherein R is an alkyl of from about 1 to about 6 carbon atoms.

9. The process of claim 8 wherein R is methyl.

10. The process of claims 1, 3, 5 or 6 wherein the solvent is selected from the group consisting of dimethylsulfoxide, sulfolane, N-methylpyrolidone, dimethylformamide.

11. The process of claim 10 wherein the solvent is dimethylsulfoxide or dimethylformamide.

12. A process for the preparation of $CF_3CH_2CH_2CH_2OH$ comprising: (1) reacting $CF_3CCl_2CH_2CH_2Cl$ with a compound of the formula $R-COO^-M^+$ wherein R is unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R', or a phenyl group unsubstituted or substituted with R'; wherein R' is an unsubstituted or substituted $C_1$ to $C_6$ straight chain or branched alkyl; and wherein when R and/or R' are substituted each is substituted with R' and M+ is a Group IA metal in the presence of a polar aprotic solvent to produce a compound of the formula $CF_3CCl=CHCH_2OC(=O)R$; (2) hydrolyzing $CF_3CCl=CHCH_2OC(=O)R$ in the presence of a solvent to produce $CF_3CCl=CHCH_2OH$; (3) reducing $CF_3CCl=CHCH_2OH$ in the presence of a reducing catalyst and a base to produce $CF_3CH_2CH_2CH_2OH$.

13. The process of claim 12 wherein $CF_3CH_2CH_2CH_2OH$ is recovered.

14. The process of claim 12 wherein the $CF_3CCl=CHCH_2OC(=O)R$ is separated prior to hydrolysis.

15. The process of claim 12 wherein M+ is selected from the group consisting of lithium, sodium and potassium.

16. The process of claim 12 wherein M+ is lithium.

17. The process of claim 12 wherein M+ is not lithium and $CF_3CCl_2CH=CH_2$ is produced as a by-product.

18. The process of claim 17 further comprising separating $CF_3CCl_2CH=CH_2$; reacting $CF_3CCl_2CH=CH_2$ with LiCl to produce $CF_3CCl=CHCH_2Cl$; reacting $CF_3CCl=CHCH_2Cl$ with a compound of the formula $R-COO^-M^+$ wherein R is unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R', or a phenyl group unsubstituted or substituted with R'; wherein R' is an unsubstituted or substituted $C_1$ to $C_6$ straight chain or branched alkyl; and wherein when R and/or R' are substituted each is substituted with R' and M+ is a Group IA metal in the presence of a polar aprotic solvent.

19. The process of claims 12 or 17 wherein R is an alkyl of from about 1 to about 6 carbon atoms.

20. The process of claim 19 wherein R is methyl.

21. The process of claims 12 or 17 wherein the polar aprotic solvent is selected from the group consisting of dimethylsulfoxide, sulfolane, N-methylpyrolidone, dimethylformamide.

22. The process of claim 21 wherein the polar aprotic solvent is dimethylsulfoxide or dimethylformamide.

* * * * *